United States Patent [19]

DiCosimo et al.

[11] Patent Number: 5,028,713

[45] Date of Patent: * Jul. 2, 1991

[54] AMMOXIDATION OF METHYL SUBSTITUTED HETEROAROMATICS TO MAKE HETEROAROMATIC NITRILES

[75] Inventors: Robert DiCosimo, Chagrin Falls; James D. Burrington, Richmond Heights; Robert K. Grasselli, Aurora, all of Ohio

[73] Assignee: The Standard Oil Company, Cleveland, Ohio

[ * ] Notice: The portion of the term of this patent subsequent to Jul. 29, 2003 has been disclaimed.

[21] Appl. No.: 925,932

[22] Filed: Nov. 3, 1986

Related U.S. Application Data

[63] Continuation-in-part of Ser. No. 559,511, Dec. 8, 1983, abandoned.

[51] Int. Cl.$^5$ ............................................. C07D 213/57
[52] U.S. Cl. ..................................................... 546/286
[58] Field of Search ......................................... 546/286

[56] References Cited

U.S. PATENT DOCUMENTS

| | | |
|---|---|---|
| 2,510,605 | 6/1950 | Porter et al. .......................... 546/286 |
| 3,555,021 | 1/1971 | Beutel et al. ...................... 548/202 X |
| 3,803,204 | 4/1974 | Grasselli et al. ................. 546/176 X |
| 3,838,068 | 9/1974 | Hagedorn et al. ..................... 502/209 |
| 3,845,094 | 10/1974 | Angstadt ....................... 260/465.3 X |
| 3,875,204 | 4/1975 | Ghirga et al. ...................... 260/465.3 |
| 3,923,819 | 12/1975 | Lussling et al. ....................... 546/286 |
| 3,927,007 | 12/1975 | Lussling et al. ....................... 546/286 |
| 3,959,297 | 5/1976 | Ishioka et al. ......................... 546/286 |
| 3,970,657 | 7/1976 | Elion et al. ............................ 546/286 |
| 3,970,659 | 7/1976 | Elion et al. ............................ 546/286 |
| 3,981,879 | 9/1976 | Elion et al. ............................ 546/286 |
| 4,001,255 | 1/1977 | Moulin et al. ......................... 546/286 |
| 4,001,316 | 1/1977 | Ishimi ................................. 502/209 X |
| 4,014,925 | 3/1977 | Ferlazzo et al. ................. 502/209 X |
| 4,017,423 | 4/1977 | White et al. ......................... 502/209 |
| 4,092,271 | 5/1978 | Sze ...................................... 502/243 |
| 4,284,781 | 8/1981 | Sze ...................................... 546/286 |
| 4,336,205 | 1/1982 | Onishi et al. .................... 546/286 X |
| 4,404,397 | 9/1983 | Daniel ............................... 260/465.3 |
| 4,444,907 | 4/1984 | Ohdan et al. .................... 502/209 X |
| 4,603,207 | 1/1986 | DiCosimo et al. ................... 546/286 |

Primary Examiner—Joseph Paul Brust
Attorney, Agent, or Firm—C. S. Lynch; D. J. Untener; L. W. Evans

[57] ABSTRACT

Disclosed is the ammoxidation of methyl substituted pyridines to make cyanopyridines using a complex metal oxide catalyst containing P, V and Mo.

7 Claims, No Drawings

AMMOXIDATION OF METHYL SUBSTITUTED HETEROAROMATICS TO MAKE HETEROAROMATIC NITRILES

This application is a continuation-in-part of Ser. No. 559,511, filed Dec. 8, 1983.

This invention relates to ammoxidation of methyl substituted heteroaromatics to make certain heteroaromatic nitriles in the presence of an oxide catalyst containing P, V and Mo.

The preparation of heteroaromatic nitriles from the corresponding methyl substituted heteroaromatic compound is known; see for example U.S. Pat. Nos. 3,555,021; 3,981,879; 3,970,657; 3,970,659; 3,923,819; 3,927,007; 4,336,205; 4,001,255; 3,959,297; 4,092,271; 3,838,068; 4,284,781 and 3,803,204. However, none of these prior art catalysts provide the combination of very high conversions coupled with very high selectivities.

It is an object of the present invention to provide a process for the production of cyanopyridines from methyl substituted pyridines in high yields coupled with high selectivities.

It is another object of the present invention to provide a novel catalyst effective in such reactions to produce high selectivities and conversions in such reactions.

Other objects, as well as aspects, features and advantages, of the invention will be apparent from a study of the specification, including the claims.

These and other objects of the present invention are realized according to the present process which comprises the ammoxidation of a methyl substituted pyridine by contacting a mixture of such a methylpyridine containing only C, H and N, to make a cyanopyridine compound by converting said methyl to cyano, with ammonia and molecular oxygen with a novel solid catalyst wherein the catalyst is a complex oxide having the elements and the amounts thereof indicated by the empirical formula $P_a V_b Mo_c M_d O_x$ wherein
M is one or any number more of Sb, Fe, W, Cu, K, Cs, B, Sn, Zr, Mn, Nb, U, Bi and Cr and
$a = 0.1-3$
$b = 0.1-6$
$a + b =$ at least 1.5
$c = 12$
$d = 0-4$, and x is a number sufficient to satisfy the valence requirements of the other elements present, said catalyst optionally containing zero to a maximum of less than 0.2 atoms of any one or more of Te, Se and Zr as oxides per 12 atoms of Mo and zero to a maximum of less than 0.5 atoms of any one or more of Fe, Co and Ni in oxide form per 12 atoms of Mo.

In the foregoing catalysts, a is usually at least 0.2; b is usually at least 0.5. Usually, also the upper value of b is 4 or less.

The catalysts of the invention as noted above can optionally be mixed with or deposited on a support such as silica, silica-alumina, alumina, titanium dioxide and the like. The active catalyst defined above can be 1-100 percent of the solid catalyst.

U.S. Pat. No. 2,510,605 discloses inter alia the ammoxidation of alpha, beta and gamma picolines with a $V_2O_5$, $MoO_3$, $P_2O_5$ catalyst. However, the ratios of V, Mo and P were very different from the present catalysts and the best reported result was 75 percent conversion and 59 percent yield of nitrile using gamma-picoline as the substrate as compared to the nearly total conversion of this compound to 4-cyanopyridine as shown in the illustrative Example 8 of the present invention hereinafter.

Temperatures, pressures, reactant ratios, diluents and contact times are not the heart of the present invention. The specific examples give some guidance relative to how to carry out the present invention. In addition, the usual conditions now recommended are 350°–460° C., usually 365°–395° C.; pressure 0.8 to 1.5 atmospheres, although higher or lower pressures can be employed; contact time, 0.1 to 20 seconds, usually 0.5 to 3 seconds; and feed ratios in moles per mole of substrate methylpyridine, 1–10 $NH_3$, usually 1.2–3; 1.2–30 molecular oxygen, usually 1.5–15, more often 2–10; and 0–150 $N_2$, often 40–100, but more economically from zero to 10. Any convenient reactor type can be used, such as a fixed bed, transport line reactor or a solid bed of catalyst flowing by gravity countercurrent to the feed gases.

Nitrogen can be replaced by another inert gas but is preferred on the basis of cost and availability, and air is a preferred source of molecular oxygen for the same reason.

By "methyl substituted" herein it is meant than an H atom of the pyridine compound on a ring carbon is substituted by the methyl radical.

Particularly valuable substrate materials for the process of the invention herein are 3-methylpyridine and 4-methylpyridine.

Normally, the catalysts of the invention are prepared by mixing the catalyst ingredients in the proper proportions in an aqueous mixture, drying the resulting aqueous slurry and calcining the product. The ingredients going into the preparation of the catalysts can be the oxides, halides, nitrates, acetates, or other salts of the particular compound added. If a support is used, the material comprising the support is usually incorporated into the catalyst along with the other ingredients. After the catalyst ingredients have been combined to form an aqueous slurry, the slurry is evaporated to dryness, and the dried solid obtained is heated in the presence of air at temperatures between about 250° and 600° C. This calcination can take place outside of the catalytic reactor or an in situ activation can be utilized.

The following examples of the invention are merely illustrative and are not to be considered as limiting.

EXAMPLE 1

Into a 1 L beaker containing 400 mL of distilled $H_2O$ was added 11.7 g (0.100 mol) of $NH_4VO_3$ and the resulting mixture heated to 80° C. with stirring. To this mixture was added 3.8 g (0.33 mol) of 85 percent $H_3PO_4$, and the mixture turned from a cloudy white suspension to a clear red solution. This solution was added at 80° C. with stirring to a mixture of 70.6 g (0.057 mol) of $(NH_4)_6Mo_7O_{24}\cdot 4H_2O$ in 250 mL of distilled $H_2O$ also at 80° C. To the resulting clear red solution was added 43.0 g of Nalco 2327 silica sol (40 percent $SiO_2$), and the resulting mixture boiled down to ca. 200 mL with vigorous stirring. When the mixture could no longer be stirred, it was heated at 120° C. for 16 hours, 290° C. for 3.0 hours, 425° C. for 16 hours, and finally at 540° C. for 4.0 hours, and the resulting brown solid ground and screened to 20-35 mesh. This catalyst has the empirical formula 80% $PV_3Mo_{12}O_x \cdot 20\%$ $SiO_2$. The $SiO_2$ is of course the support.

EXAMPLE 2

A mixture of 14.5 g (49.8 mmol) of $Sb_2O_3$ and 60 mL of 70 weight percent $HNO_3$ was heated to 80° C. with stirring for 0.5 hours, then added to a slurry of 7.8 g (67.0 mmol) of $NH_4VO_3$ in 300 mL of $H_2O$ with stirring at 80° C. The resulting mixture was added with stirring to a mixture of 70.6 g (57.1 mmol) of $(NH_4)_6Mo_7O_{24} \cdot 4H_2O$, 0.95 g (8.33 mmol) of 85 weight percent $H_3PO_4$, and 67.1 g of 30 weight percent silica sol (Ludox A.S.) in 250 mL of $H_2O$ at 80° C. Stirring and heating were continued until the mixture started to gel, then the mixture was heated at 130° C. for 16 hours, 425° C. for 16 hours, and finally at 650° C. for 3 hours. The resulting solid was ground and screened to 20-35 mesh. It was 80 percent active ingredient of the formula $P_{0.25}V_2Sb_3Mo_{12}O_x$ and 20 percent $SiO_2$ support.

The following ammoxidation runs were performed in a 5 cc. tubular steel microreactor equilibrated in a salt bath at the desired reaction temperature. The catalyst was placed in the microreactor tube between 2 layers of pyrex glass wool. The organic substrate was fed by syringe using an Orion Research Sage Pump. Air, nitrogen and ammonia flow rates were controlled by either a Brooks Dual-Channel or a Tylan Mass Flow Controller. Most runs were carried out for 2 hours, unless otherwise noted.

EXAMPLE 3

2.0 cc of 80% $PV_3Mo_{12}O_x \cdot 20\%$ $SiO_2$ catalyst of Example 1 was placed in the microreactor and equilibrated at 380° C., then a gaseous mixture of 1.0 3methylpyridine:1.5 $NH_3$:19 air:75 $N_2$ was fed through the reactor using a contact time of 2.0 seconds. The conversion of the substrate was 97 percent and selectivity to 3-cyanopyridine was 98 percent.

It should be noted that this product is of special value since it can easily be hydrolyzed to nicotinamide or to nicotinic acid as is well known.

When the foregoing was repeated but with a contact time of 2.5 seconds conversion was 99 percent and selectivity to 3-cyanopyrIdine was 95 percent In this and all other Examples the amounts of heteroaromatic nitrile product and of unreacted heteroaromatic substrate were determined by collecting the reactor effluent in a scrubber containing 10 mol of toluene at 0° C., and analyzing the resulting solution by g.c. on a 2-meter, ⅛" 10 percent Carbowax 20 M on Chromosorb W column, using o-xylene as internal standard. HCN, $NH_3$, CO and $CO_2$ were analyzed by scrubbing the reactor effluent with 10 mL of 1.0 N HCl, titrating the aqueous solution for $NH_3$ and HCN, and analyzing the scrubber effluent for CO and $CO_2$ by g.c. using a Carbowax/Molecular Sieve column.

EXAMPLE 4

A catalyst life study of the same catalyst for the same reaction and conditions as in the previous example was effected. This catalyst was used for a number of runs at 72 hours of continuous operation; initial partial loss of catalyst activity occurred during the first few hours of reaction during the first run using fresh catalyst, and therafter no further loss in catalyst activity was observed. After using the same sample of catalyst for a total of 240 hours, a contact time 3 seconds instead of 2 seconds was required to produce 97 percent selectivity at 97 percent coversion over a 72 hour period. Separate 72 hour runs at the same contact time gave reproducible results with this "aged" catalyst.

EXAMPLE 5

2.0 cc of 80% $P_{0.25}V_2Sb_3Mo_{12}O_x \cdot 20\%$ $SiO_2$ of Example 2 was placed in the microreactor and equilibrated at 380° C., then a gaseous mixture of 1.0 3-methylpyridine:1.5 $NH_3$:19 air:75 $N_2$ was fed through the reactor using a contact time of 2.0 seconds. The conversion of the 3-methylpyridine was 96 percent and selectivity to 3-cyanopyridine was 93 percent.

EXAMPLE 6

2.0 cc of 80% $PV_3Mo_{12}O_x \cdot 20\%$ $SiO_2$ catalyst of Example 1 was placed in the microreactor and equilibrated at 400°-405° C., then a gaseous mixture of 1.0 3-methylpyridine:1.6 $NH_3$:9.6 air (volume ratios) was fed through the reactor using a contact time of 8.92 seconds. The conversion of the substrate was 97 percent and selectivity to 3-cyanopyridine was 95 percent after 75 hours. After 338 hours conversion and selectivity were each 95 percent.

EXAMPLE 7

2.0 cc of 80% $P_{0.25}V_2Sb_3Mo_{12}O_x \cdot 20\%$ $SiO_2$ of Example 2 was placed in the microreactor and equilibrated at 410 C.° , then a gaseous mixture of 1.0 3-methylpyridine:1.5 $NH_3$:19 air:75 $N_2$ was fed through the reactor using a contact time of 2.0 seconds. The conversion of the 3-methylpyridine was 99 percent and selectivity to 3-cyanopyridine was 87 percent.

EXAMPLE 8

1.5 cc of 80% $P_{0.25}V_2Sb_3Mo_{12}O_x \cdot 20\%$ $SiO_2$ of Example 2 was placed in the microreactor and equilibrated at 410° C., then a gaseous mixture of 1.0 3-methylpyridine:1.5 $NH_3$:19 air:75 $N_2$ was fed through the reactor using a contact time of 1.5 seconds. The conversion of the 3-methylpyridine was 96 percent and selectivity to 3-cyanopyridine was 88 percent.

EXAMPLE 9

2.0 cc of 80% $PV_3Mo_{12}O_x \cdot 20\%$ $SiO_2$ catalyst of Example 1 was placed in the microreactor and equilibrated at 380° C., then a gaseous mixture of 1.0 4-methylpyridine:1.5 $NH_3$:19 air:75 $N_2$ was fed through the reactor using a contact time of 1.0 seconds. The conversion of the substrate was 99 percent and selectivity to 4-cyanopyridine was 98 percent.

As will be evident to those skilled in the art various modifications of this invention can be made or followed in the light of the foregoing disclosure and discussion without departing from the spirit and scope of the disclosure or from the scope of the claims.

We claim:

1. In a process for the ammoxidation of methyl substituted pyridine selected from 3-methylpyridine and 4-methylpyridine to make a cyano pyridine by converting said methyl to cyano, by contacting a mixture of said compound, molecular oxygen and ammonia in the vapor phase with a solid complex oxide catalyst, the improvement wherein the catalyst comprises the elements and the amounts thereof indicated by the empirical formula $$P_aV_bMo_cM_dO_x$$

wherein M is one or any number more of Sb, Fe, W, Cu, K, Cs, B, Sn, Mn, Zr, Nb, U, Bi and Cr and $a = 0.1-3$
$b = 0.1-6$
$a+b = $ at least 1.5
$c = 12$
$d = 0-4$, and x is a number sufficient to satisfy the valence requirements of the other elements present, said catalyst containing zero to a maximum of less than 0.2 atoms of any one or more of Te, Se and Zr as oxides per 12 atoms of Mo and zero to a maximum of less than 0.5 atoms of any one or more of Fe, Co and Ni in oxide form per 12 atoms of Mo.

2. A process of claim 1 wherein said heteroaromatic compound is 3-methylpyridine and said cyano compound is 3-cyanopyridine.

3. A process of claim 1 wherein said heteroaromatic compound is 4-methylpyridine and said cyano compound is 4-cyanopyridine.

4. In a process for the ammoxidation of a methyl substituted pyridine selected from 3-methylpyridine and 4-methylpyridine to make a cyano pyridine by converting said methyl to cyano, by contacting a mixture of said compound, molecular oxygen and ammonia in the vapor phase with a solid complex oxide catalyst, the improvement wherein the catalyst comprises the elements and the amounts thereof indicated by the empirical formula $$P_a V_b Mo_c M_d O_x$$

wherein M is one or any number of Sb, Fe, W, Cu, K, Cs, B, Sn, Mn, Zr, Nb, U, Bi and Cr and $a = 0.2-3$
$b = 0.5-4$
$a+b = $ at least 1.5
$c = 12$
$d = 0-4$, and x is a number sufficient to satisfy the valence requirements of the other elements present, said catalyst containing zero to a maximum of less than 0.2 atoms of any one or more Te, Se and Zr as oxides per 12 atoms of Mo and zero to a maximum of less than 0.5 atoms of any one or more of Fe, Co and Ni in oxide form per 12 atoms of Mo.

5. A process of claim 4 wherein said heteroaromatic compound is 3-methylpyridine and said cyano compound is 3-cyanopyridine.

6. A process of claim 4 wherein said heteroaromatic compound is 4-methylpyridine and said cyano compound is 4-cyanopyridine.

7. A process according to claim 4 wherein the catalyst contains about 0.25-1 atoms of P, 2-3 atoms of V and 0-3 atoms Sb per 12 atoms of Mo and sufficient oxygen to satisfy the valence requirements of the other elements present.

* * * * *